United States Patent [19]

Wittle et al.

[11] 4,031,071

[45] June 21, 1977

[54] TETRAPEPTIDES

[75] Inventors: Eugene Leroy Wittle; Ernest D. Nicolaides, both of Ann Arbor, Mich.

[73] Assignee: Parke, Davis & Company, Detroit, Mich.

[22] Filed: Mar. 1, 1976

[21] Appl. No.: 662,406

[52] U.S. Cl. ............... 260/112.5 LH; 260/112.5 R; 424/177
[51] Int. Cl.² ....................................... C07C 103/52
[58] Field of Search ........... 260/112.5 R, 112.5 LH

[56] References Cited
UNITED STATES PATENTS 3,725,380   4/1973   Konig et al. ................ 260/112.5 R

OTHER PUBLICATIONS

J. M. Stewart and J. D. Young, "Solid Phase Peptide Synthesis", Freeman and Co., San Francisco, 1969, pp. 9–13.
J. D. Roberts and M. C. Caserio, "Basic Principles of Organic Chemistry", Benjamin Inc., N.Y., 1965, pp. 531, 563–564.
E. Schroder and K. Lubke, "The Peptides", vol. 1, Academic Press, N.Y., 1965, pp. 79–80.

*Primary Examiner*—Delbert R. Phillips
*Attorney, Agent, or Firm*—Stephen Raines; David B. Ehrlinger; George M. Richards

[57] ABSTRACT

New tetrapeptides having the formula A-Ser(benzyl)-Try(benzyl)-D-Ala-Leu-$R_1$ wherein A is t-butoxycarbonyl, cyclohexylcarbonyl, benzyloxycarbonyl and p-nitrobenzyloxycarbonyl; Ser(benzyl) is D-Ser(benzyl) or L-Ser(benzyl); Tyr(benzyl) is D-Tyr(benzyl) or L-Tyr(benzyl); Leu is D-Leu or L-Leu, and $R_1$ is lower alkoxy, hydrazino, amino, lower alkylamino or di(-lower alkyl)amino.

4 Claims, No Drawings

TETRAPEPTIDES

SUMMARY AND DETAILED DESCRIPTION

The present invention relates to new peptide compounds that are useful as luteinizing hormone releasing factor antagonists and to methods for their production. More particularly, the invention relates to new N-protected tetrapeptides that are represented by the formula

wherein A is t-butoxycarbonyl, cyclohexylcarbonyl, benzyloxycarbonyl or p-nitrobenzyloxycarbonyl; Ser(benzyl) is L-Ser(benzyl) or D-Ser(benzyl), Tyr(benzyl) is L-Tyr(benzyl) or D-Tyr(benzyl), Leu is L-Leu or D-Leu, and $R_1$ is lower alkoxy, hydrazino, amino, lower alkylamino or di(lower alkyl)amino.

In formula I, the conventional symbols for amino acid residues of peptide compounds linked thereto are used and each is intended to have the following meaning: L-Ser(benzyl), L-seryl(benzyl); D-Ser(benzyl), D-seryl(benzyl); L-Tyr(benzyl), L-tyrosyl(benzyl); D-Tyr(benzyl), D-tyrosyl)benzyl); D-Ala, D-alanyl; L-Leu, L-leucyl; and D-Leu, D-leucyl. In addition, the term "lower alkyl" is intended to mean a straight, branched or cyclic hydrocarbon moiety of up to 6 carbon atoms, such as methyl, ethyl, isopropyl and cyclopropyl and "lower alkoxy" is intended to mean an alkoxy group having a straight, branched or cyclic hydrocarbon moiety of up to 6 carbon atoms, such as methoxy, ethoxy and isopropoxy. These symbols and terms will also be used in the formulae that follow for other compounds and each such symbol or term should be understood to have the meaning given above.

In accordance with this invention, compounds of the formula I, wherein A is as previously defined and $R_1$ is lower alkoxy, are produced by removing a protected tetrapeptide from a resin complex of the following structure

wherein said resin is a resin employed in solid phase peptide syntheses, such as those disclosed in a text by Stewart and Young, "Solid Phase Peptide Synthesis", W. H. Freeman & Company, San Francisco, 1969, which is incorporated by reference; preferably the resin is a crosslinked copolymer comprising 98 to 99 percent polystyrene crosslinked with 1 to 2 percent divinylbenzene, which is attached to the protected tetrapeptide through a methyleneoxy bridge wherein the methylene group is attached to the polymeric portion of the resin and the oxygen atom is attached to the protected tetrapeptide and A is as previously defined; by treating said resin of the formula II with a lower alkyl alcohol in the presence of tertiary amine, such as triethylamine or tripropylamine.

The resin complex is suspended in an excess of the lower alkyl alcohol, preferably methanol for periods of from about 10 hours to 4 days, preferably 16 to 24 hours, at about 15° C. to about 35° C.

While a large excess of the lower alkyl alcohol is preferred, only a catalytic amount of tertiary amine is required; however, larger amounts are preferred, such as about 10 percent volume/volume based on the amount of lower alkyl alcohol employed.

While it is not a preferred procedure, compounds of the formula I wherein $R_1$ is hydrazino, amino, lower alkylamino or di(lower alkyl)amino may be prepared by reacting compounds of the formula II wherein A is as previously defined, with hydrazine, ammonia, lower alkylamine or di(lower alkyl)amine.

The resin complex is suspended in a solvent, such as methanol, ethanol, dimethylformamide, etc., at a temperature of from about 0° to 50° C. for periods of from 12 hours to 10 days. When employing less reactive amines, the preferred solvent is dimethylformamide.

The complex resins of the formula II are prepared by coupling a protected amino acid of the formula

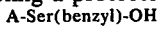

wherein A is as previously defined, with complex resins of the formula

in an organic solvent, such as dichloromethane with the aid of dicyclohexylcarbodiimide. The three reactants may be used in about equimolar quantities, but excess amounts of the protected amino acid and dicyclohexylcarbodiimide are sometimes advantageous. The reaction is generally conducted at about room temperature for a period of from about 15 minutes to about 16 hours.

The complex resins of the formula IV are prepared by treating complex resins of the formula

with a large excess of trifluoroacetic acid utilizing dichloromethane as the solvent at temperatures of from 20° to 30° C. for about 10 minutes, followed by neutralization of the trifluoroacetic acid salt with a base such as triethylamine.

The complex resins of formula V are prepared by coupling t-butoxycarbonyl-Tyr(benzyl)-OH to complex resins of the formula

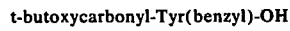  VI using the reaction procedure described for the preparation of compounds of the formula II.

The complex resins of the formula VI are prepared by treating the complex resins of the formula

with trifluoroacetic acid using the reaction procedure for the preparation of compounds of the formula IV.

The complex resins of the formula VII are prepared by coupling

to complex resins of the formula

  VIII according to the procedure used for the preparation of compounds of the formula II.

The complex resins of the formula VIII are prepared by treating the complex resins of the formula t-butoxycarbonyl-Leu-resin 
with trifluoroacetic acid using the reaction procedure for the preparation of compounds of the formula IV.

In accordance with this invention, compounds of the formula I, wherein A is as previously described and $R_1$ is hydrazino, amino, lower alkylamino or di(lower alkyl)amino are prepared by reacting a compound of the formula I wherein $R_1$ is alkoxy, preferably methoxy, with hydrazine, ammonia, lower alkylamine or di(lower alkylamine).

The reactions are conducted at temperatures of from about 5° to 100° C. for from 3 hours to 4 days, preferably about room temperature. Generally, a large excess of hydrazine, preferably used in the form of its hydrate, or amine is used (over five fold). The reaction is usually carried out in a non-reactive solvent, such as a lower alkyl alcohol, preferably methanol or ethanol, an ether such as tetrahydrofuran or dioxane, dimethylformamide or mixtures thereof.

In addition, in accordance with this invention, compounds of the formula I, wherein A is as previously defined and $R_1$ is amino, lower alkylamino or di(lower alkyl)amino are prepared by reacting a compound of the formula A-Ser(benzyl)-Tyr(benzyl)-D-Ala-Leu-N₃      IX with ammonia, lower alkylamine or di(lower alkyl) amine in a non-reactive solvent such as dimethylformamide, dioxane, tetrahydrofuran or mixtures thereof. The reaction is carried out at about −30° C. to about 0° C. for about 12 to 24 hours, preferably −20° C. to 0° C. for from 16 to 19 hours. The two reactants are used in approximately equimolar amounts although a slight excess of the amine, about 10 percent, is preferred. When A is t-butoxycarbonyl, care should be taken to avoid the presence of a large excess of acid.

The azide compounds of the formula IX are normally prepared in situ by reacting a peptide hydrazide compound of the formula I wherein A is as previously defined and $R_1$ is hydrazino, with a lower alkyl nitrite, preferably isoamyl nitrite in the presence of an acid, preferably hydrochloric acid, in an inert solvent medium such as dimethylformamide, and the resultant azide is reacted further as described above without isolation. The preferred acid for use in the azide preparation is a solution of hydrogen chloride in dimethylformamide or tetrahydrofuran; between 3 and 6 equivalents of acid are used for each equivalent of the hydrazide of formula I. The preparation of the azide is carried out at a temperature of between −30° C. and 0° C. Following the in situ formation of the azide of formula IX and prior to the further reaction of the peptide azide with the appropriate amine to form certain tetrapeptides of formula I, a tertiary amine such as triethylamine is added to the reaction mixture to neutralize the acid used.

Compounds of the formula I wherein A is as previously described and $R_1$ is hyrazino, amino, lower alkylamino or di(lower alkyl)amino are prepared by coupling a compound of the formula A-Ser(benzyl)-Tyr(benzyl)-D-Ala-Leu-OH      X with hydrazine, ammonia, lower alkylamine or di(lower alkyl)amine in an inert solvent in the presence of dicyclohexylcarbodiimide.

The above reaction is carried out using approximately equivalent amounts of reactants in a solvent such as dichloromethane, chloroform, tetrahydrofuran, dioxane or dimethylformamide, or mixtures thereof. The preferred solvent is tetrahydrofuran.

The temperature range for carrying out the reaction may be from 5° to 50° C., preferably room temperature for periods of from 10 hours to 5 days.

1-Hydroxybenzotriazole may also be used in the above reaction in addition to the dicyclohexylcarbodiimide. The 1-hydroxybenzotriazole is added in a ratio of one to two equivalents when compared to the reactants.

The compounds of the formula X are prepared by the hydrolysis of a compound of formula I wherein A is as previously defined and $R_1$ is lower alkoxy. The reaction is conducted at temperatures of from 20° to 30° C. using about 0.5 ml of the two normal aqueous sodium hydroxide solution and 10 ml. of solvent, usually water or an alcohol such as methanol, for each millimole of ester. The compound of formula X is isolated after acidification with aqueous citric acid.

Compounds of the formula
   A-Ser(benzyl)-Tyr(benzyl)-D-Ala-Leu-O-lower alkyl may also be prepared by reacting compounds of the formula A-Ser(benzyl)-OH with compounds of the formula Tyr(benzyl)-D-Ala-Leu-O-lower alkyl wherein A is as previously described. The reactants are employed in about equivalent amounts. This reaction utilizes equivalent amounts of 1-hydroxybenztriazole and dicyclohexylcarbodiimide to promote the reaction and is conducted in a solvent such as dimethylformamide. Initially the reaction is carried out at temperatures of from about 0° to −10° C. for the first few hours followed by a period of time of up to about 72 hours at room temperature. Usually the dicyclohexylcarbodiimide is added a short while after the 1-hydroxybenztriazole.

The compounds of the formula

Tyr(benzyl)-D-Ala-Leu-O-lower alkyl are prepared by treating a compound of the formula Tyr(benzyl)-D-Ala-Leu-O-lower alkyl.CF₃CO₂H with triethylamine in dimethylformamide.

The compounds of the formula

Tyr(benzyl)-D-Ala-Leu-O-lower alkyl.CF₃CO₂H are prepared by reacting a compound of the formula $N^\alpha$-t-butoxycarbonyl-Tyr(benzyl)-D-Ala-Leu-O-lower alkyl with a large excess of trifluoroacetic acid in dichloromethane for about 10 minutes at 25° C.

The compounds of the formula $N^\alpha$-t-butoxycarbonyl-Tyr(benzyl)-D-Ala-Leu-O-lower alkyl are prepared by coupling N$^\alpha$-t-butoxycarbonyl-Tyr(benzyl)-OH to compounds of the formula D-Ala-Leu-O-lower alkyl in a solvent such as dimethylformamide.

Equimolar amounts of the two reactants and dicyclohexylcarbodiimide are mixed at a temperature of about −10° C. for two hours followed by 72 hours at room temperature.

The compounds of the formula

D-Ala-Leu-O-lower alkyl are obtained by catalytically reducing compounds of the formula N$^\alpha$-benzyloxycarbonyl-D-Ala-Leu-O-lower alkyl using palladium-on-carbon and hydrogen for periods of about 2 hours at 25° C.

The compounds of the formula

N$^\alpha$-benzyloxycarbonyl-D-Ala-Leu-O-lower alkyl are produced by reacting a compound of the formula N$^\alpha$-benzyloxycarbonyl-D-Ala-OH with compounds of the formula Leu-O-lower alkyl using the procedure described above for the preparation of A-Ser(benzyl)-Tyr(benzyl)-D-Ala-Leu-O-lower alkyl.

The compounds of this invention can exist in anhydrous forms as well as in solvated, including hydrated, forms. In general, the hydrated forms and the solvated forms with pharmaceutically-acceptable solvents are equivalent to the anhydrous or unsolvated form for the purposes of the invention.

Tetrapeptides of this invention were screened for LRF antagonist activity in vitro using rat anterior pituitary cell cultures as described by Vale et al. [Endocrinology, 91, 562 (1972)]. The inhibition of LRF (luteinizing hormone release factor) induced luteinizing hormone (LH) release into the culture medium is the endpoint in this in vitro bioassay.

Following are the results of the above tests on certain preferred compounds.

| ACTIVITY TABLE FOR IN VITRO TEST IN RAT ANTERIOR PITUITARY CELL CULTURES | | | |
|---|---|---|---|
| | Molar Conc. | LH Value ng/ml. | % LH Release Inhibition |
| N$^\alpha$-t-butoxycarbonyl-O-benzyl-L-seryl-O-benzyl-L-tyrosyl-D-alanyl-L-leucine methyl ester | 5 × 10$^{-7}$ | 32.95 | 49 |
| | 1 × 10$^{-7}$ | 42.15 | 29 |
| | 5 × 10$^{-8}$ | 47.98 | 17 |
| | 1 × 10$^{-8}$ | 40.08 | 34 |
| LRF Control | 5 × 10$^{-10}$ | 56.00 | |
| Saline Control | | 8.90 | |
| | 1 × 10$^{-6}$ | 13.48 | 83 |
| LRF Control | 1 × 10$^{-9}$ | 33.10 | |
| Saline Control | | 9.33 | |
| N$^\alpha$-t-butoxycarbonyl-O-benzyl-L-seryl-O-benzyl-L-tyrosyl-D-alanyl-D-leucine N-ethylamide | 1 × 10$^{-6}$ | 19.44 | 63 |
| LRF Control | 3.5 × 10$^{-10}$ | 40.46 | |

| ACTIVITY TABLE FOR IN VITRO TEST IN RAT ANTERIOR PITUITARY CELL CULTURES -continued | | | |
|---|---|---|---|
| | Molar Conc. | LH Value ng/ml. | % LH Release Inhibition |
| Saline Control | | 6.96 | |

The luteinizing hormone releasing factor is known to be formed in the hypothalamus of mammals, from which it is released and transported by way of the hypothalamic hypophyseal portal system to the anterior pituitary, where it stimulates the secretion of luteinizing hormone. The secretion of luteinizing hormone from the anterior pituitary in turn is known to effect ovulation in experimental animals. Thus, LRF can be used to induce ovulation in animals. For a report of the structure of LRF, which has also been referred to as luteinizing hormone releasing hormone, or LH-RH, and its biological activity, see Science, Vol. 174, No. 4008, Oct. 29, 1971, pages 511–512. Thus, the tetrapeptides of this invention are useful in controlling ovulation and in restricting fertility.

The invention is illustrated by the following examples.

EXAMPLE 1

N$^\alpha$-t-Butoxycarbonyl-O-benzyl-L-seryl-O-benzyl-L-tyrosyl-D-alanyl-L-leucine methyl ester O-Benzyl-L-tyrosyl-D-alanyl-L-leucine methyl ster trifluoroacetic acid salt, 10 mmol, in 50 ml. of dimethylformamide is treated in the cold with triethylamine until alkaline to litmus. Then 10 mmol, 1.4 ml., of an additional triethylamine is added followed by 2.95 g., 10 mmol, of N$^\alpha$-t-butoxycarbonyl-O-benzyl-L-serine and 1.35 g., 10 mmol, of 1-hydroxybenztriazole. The mixture is stirred and cooled to −5° C. and is treated with 2.2 g., 10.7 mmol, of dicyclohexylcarbodiimide. The mixture is stirred in the cold for 2 to 3 hours and then at room temperature overnight. The reaction is filtered and the solid washed with dimethylformamide. The filtrate and wash is evaporated under reduced pressure and the residue is dissolved in 50 ml. of ethyl acetate and 200 ml. of ether and washed with 5 percent sodium bicarbonate solution and then with a saturated sodium chloride solution. The ethyl acetate-ether solution is dried over magnesium sulfate, filtered and evaporated. The residue is crystallized from methanol and ether giving a white solid (6.6 g.,) followed by recrystallization from methanol-ether, 6.0 g.; m.p. 67-71° C.; [α]$_D^{25}$ −1° (c 1.0, methanol).

a. O-Benzyl-L-tyrosyl-D-alanyl-L-leucine methyl ester trifluoroacetic acid salt

N$^\alpha$-t-butoxycarbonyl-O-benzyl-L-tyrosyl-D-alanyl-L-leucine methyl ester, 5.7 g., 10 mmol, in 20 ml. of dichloromethane and 50 ml. of trifluoroacetic acid are reacted together for 10 minutes at 25° C. The solution is evaporated and the residual oil used directly.

b. N$^\alpha$-t-Butoxycarbonyl-O-benzyl-L-tyrosyl-D-alanyl-L-leucine methyl ester N$^\alpha$-Benzyloxycarbonyl-D-alanyl-L-leucine methyl ester, 7 g., 20 mmol, is reduced with 500 mg. of palladium on carbon in 150 ml. of methanol by stirring the suspension under hydrogen for 2 hours at 25° C. The mixture is filtered to remove the catalyst and the solution is treated with 7.42 g., 20 mmol, of N$^\alpha$-t-butoxycarbonyl-O-benzyl-L-tyrosine and evaporated to dryness at 40° C. under reduced pressure. The residue is dissolved in 50 ml. of dimethylformamide and 2.7 g., 20 mmol, of 1-hydroxybenztriazole is added. The solution is stirred and cooled to −10° C. and 4.3 g. of dicyclohexylcarbodiimide added. The mixture is stirred with cooling (−10° C.) for 2 hours and then for 3 days at room temperature.

The solution is then filtered and the solid rinsed with dimethylformamide. The filtrate is evaporated and the residue taken into 300 ml. of ether and 50 ml. of ethyl acetate and washed with 5% sodium bicarbonate solution and with sodium chloride solution, dried over magnesium sulfate and evaporated. The residue crystallizes from ether-petroleum ether. The solid is triturated in boiling ether twice to yield 8.55 g. of a white solid, m.p. 128°–129° C.

c. $N^\alpha$-Benzyloxycarbonyl-D-alanyl-L-leucine methyl ester $N^\alpha$-Benzyloxycarbonyl-D-alanine, 8.92 g., 40 mmol, L-leucine methyl ester hydrochloride, 7.28 g., 40 mmol and 1-hydroxybenztriazole, 5.4 g., 40 mmol are dissolved in 100 ml. of dimethylformamide and the solution stirred and cooled to −10° C. Triethylamine, 5.6 ml., 40 mmol, is added and after fifteen minutes the solution is treated with 8.6 g., 42 mmol, of dicyclohexylcarbodiimide and stirred for 2 to 3 hours in a cooling bath and then to room temperature overnight. The mixture is filtered and the filtrate evaporated. The residue is dissolved in ethyl acetate and washed with 5% sodium bicarbonate solution, dilute hydrochloric acid and saturated sodium chloride solution, dried over magnesium sulfate and evaporated. The residue is crystallized twice from etherpetroleum ether, 12.88 g.; m.p. 65°–68° C.

d. $N^\alpha$-Benzyloxycarbonyl-D-alanine

D-alanine is reacted (12.5 g., 0.14 mol) with 26 g., 0.14 mol + 2 g. excess. of benzyloxycarbonyl chloride and 0.28 mol of sodium hydroxide. The D-alanine is dissolved in one equivalent of sodium hydroxide solution, cooled in ice, and treated slowly with the acid chloride and the second equivalent of sodium hydroxide while maintaining pH 10–12. The reaction is stirred for an additional hour with cooling and is worked up by extraction with ether and acidification of the aqueous solution. A precipitate soon solidifies and is collected and dried; 23.5 g.; m.p. 82°–85° C.

EXAMPLE 2

$N^\alpha$-t-Butoxycarbonyl-O-benzyl-L-seryl-O-benzyl-L-tyrosyl-D-alanyl-L-leucine N-ethylamide The methyl ester of Example 1, 747 mg., 1 mmol, is dissolved in methanol, 5 ml. and dimethylformamide, 1 ml., and treated with ethylamine, 5 ml., at 25° C. for 7 days. The methanol and excess amine are removed by evaporation and the product is crystallized from 5 ml. of methanol and 50 ml. of ether; 660 mg.; m.p. 180°–183° C.

EXAMPLE 3

$N^\alpha$-t-Butoxycarbonyl-O-benzyl-L-seryl-O-benzyl-L-tyrosyl-D-alanyl-D-leucine N-ethylamide $N^\alpha$-t-Butoxycarbonyl-O-benzyl-L-seryl-O-benzyl-L-tyrosyl-D-alanyl-D-leucine methyl ester, 590 mg., 0.79 mmol, methanol, 30 ml., and ethylamine, 10 ml., are let stand in a closed container for several days at room temperature. When the reaction is complete as shown by thin layer chromatography, the volatile components are removed and the product crystallized from petroleum ether, 0.55 g.; $[\alpha]_D^{25}$ −7.2° (c 1.0, DMF).

a. $N^\alpha$-t-Butoxycarbonyl-O-benzyl-L-seryl-O-benzyl-L-tyrosyl-D-alanyl-D-leucine methyl ester $N^\alpha$-t-Butoxycarbonyl-O-benzyl-L-seryl-O-benzyl-L-tyrosyl-D-alanyl-D-leucine resin, 10 g., is first washed with ethanol then dried at 50° C. under reduced pressure. The dried resin is stirred overnight with 50 ml. of dimethylformamide, 20 ml. of triethylamine and 150 ml. of methanol. The reaction mixture is filtered and the filtrate evaporated under reduced pressure. The product is crystallized from isopropanol and washed with petroleum ether and ether; 1.42 g., m.p. 131°–135°; $[\alpha]_D^{23}$ + 0.5° (c 1.01, DMF).

b. $N^\alpha$-t-Butoxycarbonyl-O-benzyl-L-seryl-O-benzyl-L-tyrosyl-D-alanyl-D-leucine resin The N-t-butoxycarbonyl-O-benzyl-L-tyrosyl-D-alanyl-D-leucine resin is agitated with 300 ml. of 50 percent trifluoroacetic acid in dichloromethane, filtered and washed three times with 250 ml. of dichloromethane. $N^\alpha$-t-butoxycarbonyl-O-benzyl-L-serine, 11.29 g., 37 mmol, is added in dichloromethane, 250 ml., and the mixture agitated for thirty minutes followed by the addition of dicyclohexylcarbodiimide, 7.62 g., 37 mmol and agitated for eighteen hours. The resin is filtered and washed three times with dichloromethane and finally with ethanol before drying.

c. N-t-Butoxycarbonyl-O-benzyl-L-tyrosyl-D-alanyl-D-leucine resin $N^\alpha$-t-butoxycarbonyl-D-alanyl-D-leucine resin, 44 g., 35.6 mmol, is agitated with 300 ml. of 50 percent trifluoroacetic acid in dichloromethane, filtered and washed three times with 250 ml. of dichloromethane. $N^\alpha$-t-butoxycarbonyl-O-benzyl-L-tyrosine 13.8 g., 37 mmol is added in dichloromethane, 250 ml., and the mixture agitated for 30 minutes followed by the addition of dicyclohexylcarbodiimide, 7.62 g., 37 mmol, and agitation for 18 hours. The resin is filtered and washed three times with dichloromethane and finally with ethanol before drying.

d. $N^\alpha$-t-Butoxycarbonyl-D-alanyl-D-leucine resin $N^\alpha$-t-Butoxycarbonyl-D-leucine resin (53 g., 42.9 mmol) is deprotected as in part (b), and $N^\alpha$-t-butoxycarbonyl-D-alanine (8.5 g., 45 mmol) is added followed by the addition of dicyclohexylcarbodiimide, 9.3 g., 45 mmol in chloroform, after 15 to 30 minutes, followed by agitation for 18 hours. The product is separated by filtration and washed three times with dichloromethane, 250 ml., and dried.

e. $N^\alpha$-t-Butoxycarbonyl-D-leucine resin 15.8 g., 68.4 mmol, of $N^\alpha$-t-butoxycarbonyl-D-leucine, 50 g. of chloromethylated resin and 6.5 g., 64.3 mmol of triethylamine are stirred for several days at 25° C. and filtered, washed with ethanol, water, methanol, dichloromethane, ether and dried. Nitrogen analysis shows 0.782 mmol per gram.

We claim:

1. A tetrapeptide represented by the formula
A-Ser(benzyl)-Tyr(benzyl)-D-Ala-Leu-R₁ wherein A is t-butoxycarbonyl, cyclohexylcarbonyl, benzyloxycarbonyl or p-nitrobenzyloxycarbonyl; Ser(-benzyl) is L-Ser(benzyl) or D-Ser(benzyl), Tyr(benzyl) is L-Tyr(benzyl) or D-Tyr(benzyl), Leu is L-Leu or D-Leu, and $R_1$ is lower alkoxy, hydrazino, amino, lower alkylamino or di(lower alkyl)amino.

2. The compound of claim 1 having the name $N^\alpha$-t-butoxycarbonyl-O-benzyl-L-seryl-O-benzyl-L-tyrosyl-D-alanyl-L-leucine methyl ester.

3. The compound of claim 1 having the name $N^\alpha$-t-butoxycarbonyl-O-benzyl-L-seryl-O-benzyl-L-tyrosyl-D-alanyl-L-leucine N-ethylamide.

4. The compound of claim 1 having the name $N^\alpha$-t-butoxycarbonyl-O-benzyl-L-seryl-O-benzyl-L-tyrosyl-D-alanyl-D-leucine N-ethylamide.

* * * * *